(12) United States Patent
Cohen et al.

(10) Patent No.: US 7,883,851 B2
(45) Date of Patent: Feb. 8, 2011

(54) COMMON ALLELE ON CHROMOSOME 9 ASSOCIATED WITH CORONARY HEART DISEASE

(75) Inventors: Jonathan C. Cohen, Dallas, TX (US); Helen H. Hobba, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 440 days.

(21) Appl. No.: 11/751,563

(22) Filed: May 21, 2007

(65) Prior Publication Data

US 2008/0274460 A1 Nov. 6, 2008

Related U.S. Application Data

(60) Provisional application No. 60/927,361, filed on May 2, 2007.

(51) Int. Cl.
C12Q 1/68 (2006.01)
C12P 19/34 (2006.01)

(52) U.S. Cl. .......................................... 435/6; 435/91.2

(58) Field of Classification Search .................. None
See application file for complete search history.

(56) References Cited

U.S. PATENT DOCUMENTS

| | | | |
|---|---|---|---|
| 2007/0015170 | A1 | 1/2007 | Salonen et al. |
| 2007/0065865 | A1 | 3/2007 | Carlton et al. |
| 2007/0072798 | A1 | 3/2007 | Salonen et al. |
| 2007/0072821 | A1 | 3/2007 | Iakoubova et al. |
| 2007/0128597 | A1 | 6/2007 | Schwers et al. |
| 2009/0150134 | A1 | 6/2009 | De Leon et al. |

FOREIGN PATENT DOCUMENTS

| | | |
|---|---|---|
| WO | WO 2004/035746 | 4/2004 |
| WO | WO 2006/040409 | 4/2006 |
| WO | WO 2007/006862 | 1/2007 |
| WO | WO 2008/102380 | 8/2008 |

OTHER PUBLICATIONS

NCBI Single Nucleotide Polymorphism database, submitted SNP(ss) details: ss15539811, obtained from http://www.ncbi.nlm.nih.gov/projects/SNP/snp_ss.cgi?subsnp_id=15539811, Sep. 8, 2009, seven pages.*

NCBI Single Nucleotide Polymorphsim database, Method Detail, Method ID CHR9_12_NA07340, obtained from http://www.ncbi.nlm.nih.gov/projects/SNP/snp_viewTable.cgi?mid=1212, Sep. 8, 2009, two pages.* dbSNP sample individual Report for dbSNP individual 5205. Accessed from http://www.ncbi.nlm.nih.gov/projects/SNP/snp_ind.cgi?ind_id=5205 on Aug. 4, 2010, one page.*

Database DBSNP Accession No: ss66599780, "Genotyping assay for SNP rs10116277" dated Nov. 11, 2006.

Database DBSNP Accession No: ss66710789, "Genotyping assay for SNP rs2383207" dated Nov. 11, 2006.

Database DBSNP Accession No: ss66735836, "Genotyping assay for SNP rs1333040" dated Nov. 11, 2006.

Database DBSNP Accession No. ss43784416, "Genotyping assay for SNP rs10757278" dated Jul. 18, 2005.

deCODE Launches deCODE MI™—A Test for a Major Genetic Factof for Early-onset Heart Attack. Oct. 10, 2007, Biomedicine, "http://www.bio-medicine.org/medicine-technology-1/deCODE-Launches-deCODE-MI-28TM-29—A-Test-for-a-Major-Genetic-Risk-Factor-for-Early-onset-Heart-Attack-494-2/".

deCODE Launches deCODEMI ™—A Test for Major Genetic Risk Factor for Early-onset Heart Attack, Oct. 11, 2007, CnnMoney.com, http://money.cnn.com/news/newsfeeds/articles/prnewswire/NTTH005111020007-1.htm.

Empowering Prevention , 2007, "http://www.decodediagnostics.com/MI-genetics.php ".

International HapMap Consortium, 2005, "A haplotype map of the human genome" Nature 437(7063): 1299-1320.

International HapMapProject (HAPMAP), "Showing 58.09 kbp from chr9, positions 22, 062,301 to 22,120,389," Available Online Jun. 30, 2007 at http://www.hapmap.org/cgi-perl/gbrowse/hapmap3_B36/ (pp. 1-3).

PCT International Search Report and Written Opinion, dated Nov. 26, 2008, in related PCT Application No. PCT/US08/05751.

The Welcome Trust Case Control Consortium, 2007, "Genome-Wide Association Study of 14,000 Cases of Seven Common Diseases and 3,000 Shared Controls." Nature 447: 661-678 Supplementary Information, p. 1-56 (http://www.nature.com/nature/journal/v447/n7145/extref/nature05911-s1.pdf).

Topol, Eric J. Feb. 13, 2008, "The 9p21 Story—What's All the Excitement About?" Medscape Genomic Medicine http://www.medscape/com/viewarticle/569496.

WHAT is deCode MI™, 2007, "http://www.decodediagnostics.com/MI.php".

Helgadottir et al., "A Common Variant on Chromosome 9p21 Affects the Risk of Myocardial Infarction", Science, vol. 316, Jun. 8, 2007, pp. 1491-1493.

Helgadottir et al., Supporting Online Material for "A Common Variant on Chromosome 9p21 Affects the Risk of Myocardial Infaraction", Science Express, May 3, 2007.

McPherson et al., "A Common Allele on Chromosome 9 Associated with Coronary Heart Disease", Science, vol. 316, Jun. 8, 2007, pp. 1488-1491.

McPherson et al., Supporting Online Material for "A Common Allele on Chromosome 9 Associated with Coronary Heart Disease", Science Express, May 3, 2006.

(Continued)

*Primary Examiner*—Juliet C Switzer
(74) *Attorney, Agent, or Firm*—Richard Aron Osman (57) ABSTRACT

Disclosed are methods and compositions for determining whether a person carries an allele associated with increased risk for coronary atherosclerosis by determining whether the person has had RA-CHR9 allele, such as by determining whether the person has an RA-CHR9 allele-associated single nucleotide polymorphism (SNP).

29 Claims, 1 Drawing Sheet

OTHER PUBLICATIONS

Samani et al., "Genomewide Association Analysis of Coronary Artery Disease", N. Engl. J. Med., vol. 357, No. 5, Aug. 2, 2007, pp. 443-453.

Shen et al., "Association Betwen Four SNPs on Chromosome 9p21 and Myocardial Infarction is Replicated in an Italian Population", J. Hum. Genet., vol. 53, 2008, pp. 144-150.

Shen et al., "Four SNPs on Chromosome 9p21 in a South Korean Population Implicate a Genetic Locus that Confers High Cross-Race Risk for Development of Coronary Artery Disease", Arterioscler. Thromb. Vasc. Biol., vol. 28, 2008, pp. 360-365.

Wang et al., "Premature Myocardial Infarction Novel Susceptibility Locus on Chromosome 1P34-36 Identified by Genomewide Linkage Analysis", Am. J. Hum. Genet., vol. 74, 2004, pp. 262-271.

The Wellcome Trust Case Control Consortium, "Genome-Wide Association Study of 14,000 Cases of Seven Common Diseases and 3,000 Shared Controls", Nature, vol. 447, Jun. 7, 2007.

* cited by examiner

Fig. 1

COMMON ALLELE ON CHROMOSOME 9 ASSOCIATED WITH CORONARY HEART DISEASE

CROSS-REFERENCE TO RELATED APPLICATION

This application claims priority to U.S. Prov Appl No. 60/927,361 filed May 2, 2007.

BACKGROUND OF THE INVENTION

The field of the invention is an allele on chromosome 9 associated with coronary heart disease.

Coronary heart disease (CHD) is a major cause of death in Western countries. Here we used genome-wide association scanning to identify a 58 kilobase interval near the INK locus on chromosome 9 that was consistently associated with CHD in six independent samples (n>23,000 participants) from four Caucasian populations. The interval contains no annotated genes and is not associated with established CHD risk factors such as plasma lipoproteins, hypertension or diabetes. Homozygotes for the risk allele comprise 20-25% of Caucasians and have a ~30-40% increased risk of CHD.

SUMMARY OF THE INVENTION

The invention provides methods and compositions for determining whether a person carries an allele associated with increased risk for coronary atherosclerosis, the method comprising the step of: determining whether the person has an RA-CHR9 allele.

In particular embodiments, the determining step comprises detecting the allele using a method selected from the group consisting of: mass spectroscopy, oligonucleotide microarray analysis, allele-specific hybridization, allele-specific PCR, and sequencing.

In particular embodiments, the determining step comprises determining whether the person has an RA-CHR9 allele-associated single nucleotide polymorphism (SNP), particularly SNP selected from the group consisting of rs10757274 and rs2383206, rs6475606, rs1412832, rs10811645, rs7865618.

In particular embodiments, the person has a family history of coronary atherosclerosis.

In particular embodiments, the method further comprises the step of treating the person characterized for increased risk for coronary atherosclerosis with therapy to delay onset of or slow progression of the coronary atherosclerosis, particularly wherein the therapy comprises a lipid-lowering medication.

In another embodiment, the invention provides reagents and kits for practicing the disclosed methods.

BRIEF DESCRIPTION OF THE FIGURE

FIG. 1. Fine mapping of the genomic interval on chromosome 9 associated with coronary heart disease. Panel A. SNPs spaced ~5 kb apart in the interval extending 175 kb upstream and downstream of rs10757274 and rs2383206 were assayed in 500 cases and 500 controls from the Ottawa Heart Study population. Bars represent P values (determined using Chi-Square tests) for differences in allele frequency between cases and controls. Arrowheads indicate rs10757274 and rs2383206. The asterisk represents rs518394. The risk interval is indicated with a gray box. The linkage disequilibrium map indicates pairwise $r^2$ values. Blocks are shaded on a continuous scale where white represents an $r^2$ of 0 and black represents an $r^2$ of 1. Panel B. Physical map of the region showing the location of the risk interval (gray box) relative to the noncoding RNA DQ485453 and adjacent genes: CDKN2A, ARF, and CDKN2B. Arrowheads indicate rs10757274 and rs2383206 and the asterisk represents rs518394 (see Panel A).

DETAILED DESCRIPTION OF SPECIFIC EMBODIMENTS OF THE INVENTION

The invention provides methods and compositions for determining whether a person carries an allele associated with increased risk for coronary atherosclerosis, the method comprising the step of: determining whether the person has an RA-CHR9 allele, a 58 kb region (extending from 22,062,301 to 22,120,389 of chromosome 9) significantly associated with CHD, as detailed below.

The RA-CHR9 allele may be detected by any suitable, specific technique known in the art, such as mass spectroscopy, oligonucleotide microarray analysis, allele-specific hybridization, allele-specific PCR, and sequencing. In one embodiment, the determining step comprises determining whether the person has an RA-CHR9 allele-associated single nucleotide polymorphism (SNP). Suitable SNPs are described below, and alternative suitable RA-CHR9 allele-associated SNPs are readily identified as described below.

In particular embodiments, the person subject to evaluation has a family history of coronary atherosclerosis.

In particular embodiments, the method further comprises the step of treating the person characterized for increased risk for coronary atherosclerosis with therapy to delay onset of or slow progression of the coronary atherosclerosis, particularly wherein the therapy comprises a lipid-lowering medication.

In another embodiment, the invention provides reagents and kits for practicing the disclosed methods.

Examples

Coronary heart disease (CHD) is the single greatest cause of death worldwide (1, 2). Although CHD is highly heritable, the DNA sequence variations that confer cardiovascular risk remain largely unknown. To identify sequence variants associated with CHD, we undertook a genome-wide association study using 100,000 single nucleotide polymorphisms (SNPs). To minimize false positive associations without unduly sacrificing statistical power, the study design comprised three sequential case-control comparisons performed at a nominal significance threshold of P<0.025 (Table 1). For the initial genome-wide scan, cases and controls were Caucasian men and women from Ottawa, Canada who participated in the Ottawa Heart Study (OHS). Cases had severe, premature CHD with a documented onset before the age of 60 years and culminating in coronary artery revascularization. To limit confounding by factors that strongly predispose to premature CHD, individuals with diabetes or plasma cholesterol levels consistent with monogenic hypercholesterolemia (>280 mg/dL) were excluded. Controls were healthy Caucasian men (>65 y) and women (>70 y) from Ottawa who had no symptoms or history of CHD.

Custom oligonucleotide arrays (3) were used to assay 100,000 SNPs arranged at approximately 30 kb intervals throughout the genome in 322 cases and 312 controls (OHS-1). Of these, 9,636 SNPs deviated strongly from Hardy-Weinberg equilibrium (P<0.001) or did not meet quality-control criteria (3) and 17,500 were sub-polymorphic (minor allele frequency<1%) in the sample. The remaining 72,864 SNPs were entered into the analysis and 2,586 were associated with CHD at a nominal significance threshold of 0.025. These 2,586 SNPs were genotyped in an independent sample of 311 cases and 326 controls, from Ottawa (OHS-2) using the same criteria as OHS-1. Of these, 50 were associated with CHD at a nominal significance threshold of 0.025, with the same direction of effect.

To limit attrition of true positive associations due to inadequate statistical power, the third case-control comparison was performed in a much larger prospective study of CHD risk, the Atherosclerosis Risk in Communities (ARIC) study, which enrolled and followed 11,478 Caucasians (4). Only two of the 50 SNPs identified in the Ottawa cohorts were significantly associated with incident CHD in the ARIC population. These two SNPs, rs10757274 and rs2383206, were located within 20 kb of each other on chromosome 9 and were in strong linkage disequilibrium ($r^2$=0.89).

To validate the association between rs10757274 and rs2383206 and CHD, both SNPs were assayed in three additional independent cohorts: the Copenhagen City Heart Study (CCHS), a prospective study of ischemic heart disease in 10,578 Danish men and women (5); the Dallas Heart Study (DHS), a population-based probability sample of Dallas County residents (6); and a third sample of 647 cases and 847 controls from the Ottawa Heart Study population (OHS-3). In the CCHS, cases were participants who experienced an ischemic cardiovascular event during the 20 yr follow-up period while controls were those who did not develop CHD over the same time interval. In the DHS, cases and controls were defined using electron-beam computer tomography to measure coronary artery calcium, an index of coronary atherosclerosis (7). In OHS-3, cases had documented CHD before the age of 55 (men) or 65 (women) years, whereas controls were men aged >65 and women aged >70 years who did not have symptoms of CHD. In all three validation studies, both SNPs were significantly associated with CHD (Table 2).

The magnitude of CHD risk associated with the risk allele was determined by Cox proportional-hazards modeling in the ARIC and CCHS cohorts. The hazard ratios associated with the risk alleles were comparable in the two populations, and indicated a graded increase in risk from noncarriers to heterozygotes to homozygotes (Table 3). The two SNPs (rs10757274 and rs2383206) define an allele that was associated with a ~15-20% increase in risk in the 50% of individuals who were heterozygous for the allele and a ~30-40% increase in CHD in the 25% of Caucasians who were homozygous for the allele. The population attributable risk associated with the risk allele was 12.5-15% in the ARIC population and 10-13% in the CCHS cohort.

The finding that the risk allele was associated with coronary artery calcification in the DHS and with severe premature atherosclerosis in OHS-1 indicates that it promotes CHD by increasing the atherosclerotic burden. The risk allele was not associated with any of the major risk factors for atherosclerosis in ARIC or CCHS, and the association remained significant in models that considered multiple possible confounding covariates (including age, gender, plasma lipid levels, blood pressure, diabetes, and plasma C-reactive protein levels). These analyses indicates that the effect of the chromosome 9 risk allele on CHD was not mediated by any of the established risk factors for cardiovascular disease.

Figure 1:
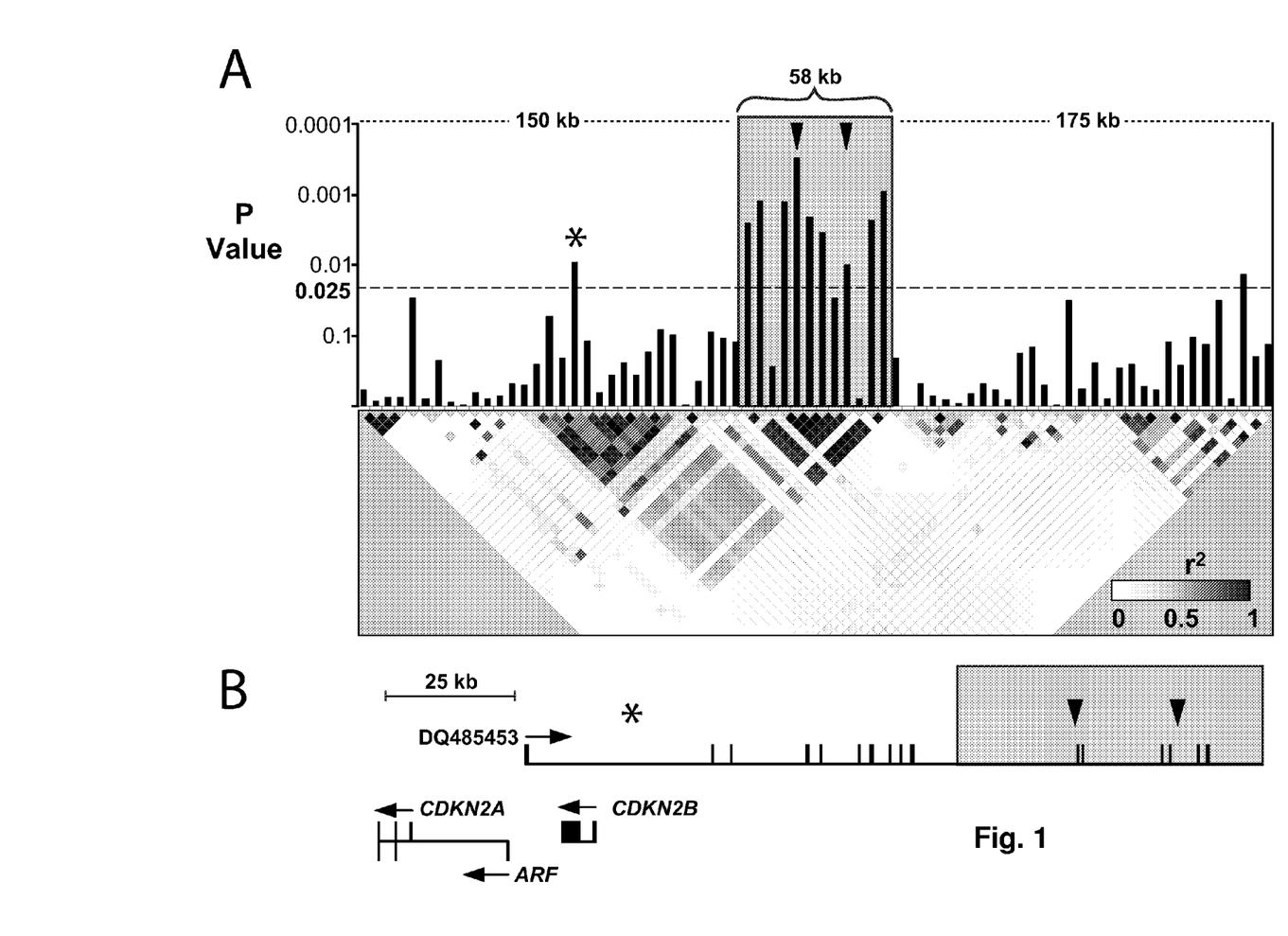

To fine-map the locus associated with CHD, we assayed SNPs spaced at ~5 kb intervals across the region extending 175 kb upstream and downstream of rs10757274 and rs2383206 in 500 cases and 500 controls from OHS-2 and OHS-3. Eight additional SNPs at the locus spanning a 58 kb region (extending from 22,062,301 to 22,120,389) were significantly associated with CHD (FIG. 1). All eight were in strong linkage disequilibrium with each other and with rs10757274 and rs2383206. The region demarcated by these SNPs was flanked on both sides by ~50 kb regions in which none of the 30 SNPs tested were associated with CHD. Two of 65 SNPs in the 350 kb region surrounding the 58 kb risk locus were associated with CHD at the nominal significance threshold, but neither was in strong linkage disequilibrium with rs10757274 and rs2383206. These data indicate that the risk allele comprises a single haplotype that spans ~58 kb.

Inspection of the UCSC Genome Browser and BLAST searches against the NCBI nr nucleotide sequence database revealed no annotated genes or microRNAs within the 58 kb interval. A number of spliced ESTs map within the interval, but none contain open reading frames that extend more than a few amino acids. Resequencing of the 58 kb interval in two homozygotes for the risk allele and one homozygote for the reference allele revealed 66 polymorphisms (SNPs plus small insertions or deletions), of which 35 were specific to the risk allele (Table 4). Only one of these variants, a copy number variation in a run of 9 consecutive CAT repeats (extending from nucleotide 22110787 to 22110814, NCBI build 36.1) mapped to a spliced transcript (BI765545) that appears to be part of a large noncoding RNA of unknown function (8). PCR amplification of cDNAs confirmed expression of the transcript in placenta and transformed lymphocytes. Variation in the expression or function of this transcript may be associated with risk of CHD.

Alternatively the risk allele may alter a regulatory element that affects the expression of a gene located outside of the 58 kb interval. Cross-species sequence alignments revealed several conserved segments within the 58 kb interval that may contain such regulatory elements. It is also possible that the risk allele extends beyond the 58 kb interval defined in this study, and that the functional sequence variants that confer risk of CHD are located outside of the interval. Resequencing the coding regions of the two genes most proximal to the risk locus, CDKN2A and CDKN2B revealed only a single variant (A158S in CDKN2A) that was present in 6 of the 96 individuals examined and is thus unlikely to explain the CHD risk associated with the locus. The localization of the risk locus to a region devoid of known genes implicates a previously unrecognized gene or regulatory element that can substantially affect CHD independently of established risk factors.

Comparison of the Yoruba and CEPH data from the HapMap revealed striking ethnic differences in allele frequencies in the risk interval (Table 5). Of the 10 alleles that were significantly associated with CHD in whites, 3 were virtually absent from the Yoruba population, and 6 others much less common. Both rs10757274 and rs2383206 were present at appreciable frequencies among African-Americans in ARIC and DHS, but neither SNP was associated with CHD in either population (Table 6). The apparent ethnic differences in association between these SNPs and CHD in ARIC may reflect differences in statistical power in ARIC, but cannot explain the ethnic differences observed in DHS, where African-Americans are the largest group, indicating that the functional sequence variants associated with the risk allele in whites are less common in African-Americans. This notion is consistent with our finding that the frequencies of several alleles associated with CHD risk factors differ widely among ethnic groups (9-11).

The results of this study illustrate both the perils and the promise of whole-genome association. The initial scan and the first replicate screen both generated substantially more SNPs that achieved the pre-specified significance threshold than would be predicted by chance alone, as indicated by permutation testing. Yet only two of these SNPs (comprising one allele) survived further replication, despite the use of a large sample (i.e. ARIC) with high statistical power. This finding highlights the necessity for adequate replication to protect against artifacts that may occur due to population stratification, multiple testing, or other factors to which whole-genome association studies are particularly susceptible. The consistent replication of the chromosome 9 risk allele in six independent study samples indicates that the approach can be productively applied to conditions as complex as CHD, which is known to be influenced by a variety of environmental and genetic factors (12). Furthermore, analysis of 50 randomly selected regions of 500 kb each indicated that the 72,864 informative SNPs used in the initial scan provided 30-40% of the power that would be obtained by assaying all Phase II Hapmap SNPs.

The examples and detailed description herein are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Supplementary Material; Materials and Methods: Study Populations

The Ottawa Heart Study. The Ottawa Heart Study is an ongoing, hospital-based study of coronary heart disease at the Ottawa Heart Institute in Ottawa, Canada. The study was approved by the Institutional Review Board at the University of Ottawa Heart Institute and all participants provided written informed consent. All patients at the Institute who undergo coronary artery bypass grafting, coronary artery angiography, or care for acute myocardial infarction are invited to participate in the study. Three independent samples (OHS-1, OHS-2, and OHS-3) were ascertained serially for this study. Caucasian men and women aged <60 y with advanced disease requiring coronary artery bypass grafting or percutaneous coronary intervention who did not have a history of diabetes mellitus or severe dyslipidemia, suggestive of a monogenic lipid disorder (TC>280 mg/dl/7.0 mmol/L) were included in the initial genome-wide scan (OHS-1). Subsequently, a second sample of individuals was recruited using the same clinical criteria (OHS-2). The mean age of onset of CAD in these individuals was 47.8+7.5(SD) years. Once recruitment for OHS-1 and OHS-2 was completed, individuals with documented CHD before the age of 55 (men) or 65 (women) were recruited for OHS-3. Healthy elderly controls (men>65 y, women>70 y) were recruited via an extensive newspaper and television advertising campaign in the Ottawa community. Controls were carefully interviewed by a physician or nurse to ascertain that they were free of symptoms of possible ischemic arterial disease and had no past history of cardiovascular symptoms, a positive stress test, coronary angiography demonstrating stenosis (>50%) in any artery or clinical cardiovascular events. Individuals with the same ethnic background as the cases (Caucasian) were included in this study. The mean age of the control subjects was 74.9+4.8 years. Controls for OHS-1, OHS-2, and OHS-3 were collected sequentially as described for cases.

The Atherosclerosis Risk in Communities Study (ARIC). The ARIC study comprised men and women aged 45 to 64 years who were randomly selected from four communities (Jackson, Miss.; Minneapolis Minn.; Forsyth County, N.C.; and Washington County, Md.). The protocol for the study was approved by the institutional review boards of all centers, and all participants provided written informed consent that included consent for genetic studies. Race or ethnic group was determined by self-identification; participants described themselves as black or white in response to a questionnaire on which the available categories were "black", "white", "Indian", or "Asian". Plasma lipids, glucose, insulin and lipoproteins were assayed in the ARIC central lipid laboratory with commercial reagents, as previously described (S1-S3). Cases had a documented CHD event (defined as myocardial infarction, coronary artery revascularization, or coronary death) during the 15 yr follow-up period of the study; individuals with prevalent disease at the baseline visit were excluded. Controls were individuals who did not develop incident CHD. The study sample delineated by these criteria provides >90% power to detect common alleles (minor allele frequency >0.1) that differ in frequency by 0.06 or more between cases and controls.

The Copenhagen City Heart Study (CCHS). The Copenhagen City Heart Study population was randomly drawn from the Copenhagen Population Register in January 1976 (S4). The study was approved by the Danish ethics committee for the City of Copenhagen and Frederiksberg and informed consent was provided according to the Declaration of Helsinki. The sample was drawn from a population of approximately 90 000 inhabitants 20 years and older living within 10 wards surrounding Rigshospitalet, the National University Hospital of Copenhagen. A second examination was performed 5 years later (1981-1983), and a third examination was performed after 15 years (1991-1994), at which time blood samples were obtained from 9,259 individuals for isolation of DNA. A self-administered questionnaire was used to obtain information regarding familial history, education and socio-economic status, and smoking and drinking habits. Plasma cholesterol and triglyceride levels were determined enzymatically using commercial reagents, and HDL-C was determined after removal of apoB-containing lipoproteins by precipitation with phosphotungstic acid and magnesium. Participants were white and of Danish descent.

The Dallas Heart Study. The Dallas Heart Study is a multi-ethnic, population-based probability sample of Dallas County residents. The study was approved by the Institutional Review Board at the University of Texas Southwestern Medical Center and included three phases: an in-home interview, an in-home phlebotomy visit, and a clinic visit during which a variety of imaging examinations were performed. Caucasian men and women who underwent electron-beam computer tomography to assess coronary artery calcification were eligible for the present study. Each individual underwent two consecutive scans. The distribution of CAC scores is extremely skewed and inter-scan variability is high for scores below 10 Agatston units (5), therefore we excluded individuals with CAC scores between 2 and 10 units and divided the population into controls (CAC scores of ≦2 units, n=575) and cases (those with CAC scores ≧10 units, n=166), as previously described (S5).

Genotyping: Chip-Based Oligonucleotide Hybridization: SNP Selection.

Using NCBI Build 34, the genome was partitioned into blocks of 13 kb, and one SNP was selected from each block. Using a whole-genome multi-ethnic haplotype map (S6), we preferentially chose common haplotype defining SNPs, then common SNPs, then rare SNPs. Where no previously characterized SNPs were available, we chose validated SNPs from dbSNP. Ties were broken so as to minimize variation in inter-SNP spacing. This yielded roughly 200,000 SNPs, of which 70% were haplotype defining, and another 10% were common, 4% were rare, and 16% were from dbSNP. Every other SNP was selected, yielding a set of ~100,000. Using performance data for these assays on another array design to identify failing assays, we selected replacement SNPs from the multi-ethnic map to fill the largest gaps.

Genotyping. Genotyping was performed by Perlegen Sciences using custom high-density oligonucleotide arrays. Each SNP was interrogated by 24 different 25mer oligonucleotide probes synthesized on a glass substrate. The 24 features comprise four sets of six features interrogating both reference and alternate alleles on forward and reference strands. Each allele and strand is represented by oligonucleotides with the variant nucleotides a five offset positions: 22, 21, 0, 1 and 2, (where the number indicates the position of the SNP within the 25mer, with 0 being the 13th base). At offset 0, a quartet was tiled, which includes the perfect match to reference and alternate SNP alleles and the two remaining nucleotides as mismatch probes. When possible, the mismatch features were selected to match a purine nucleotide substitution with a purine nucleotide and a pyrimidine nucleotide with a pyrimidine nucleotide.

The reliability of the intensity measurements of each SNP was assessed using two methods. One metric, "conformance", indicates the presence of specific target DNA for that SNP. The other metric, "signal to background ratio", measures the relative amounts of specific and nonspecific binding. SNPs that failed to meet specified cutoffs on both metrics were discarded. Conformance was computed independently for the two allele feature sets, and a maximum was taken of the two values. Conformance of a given allele is defined as the fraction of feature sets for which the perfect-match feature is brighter than the corresponding mismatch feature. SNP measurements having conformance scores <0.9 were discarded. The signal to background ratio was calculated from intensity measurements for both alleles, as the root mean square of trimmed mean intensities for the perfect-match features for each allele, divided by the corresponding value for the mismatch features. SNP measurements having signal/background <1.5 were discarded.

Calling Algorithm. Individual genotypes for a SNP were determined by clustering measurements from multiple scans in the two-dimensional space defined by background-adjusted trimmed mean intensities of the perfect-match features for each allele. A K-means algorithm was used to assign measurements to clusters representing distinct diploid genotypes. The average call rate was 98.54 percent.

Mass Spectrometry. The 50 sequence variants identified in the genome-wide scan were assayed in the ARIC population by mass spectrometry using the Sequenom MassARRAY system (Sequenom, Inc.; San Diego, Calif.).

Fluorogenic 5'-nucleotidase assays for rs10757274 and rs2383206 were developed with the use of the TaqMan assay system (Applied Biosystems). The assays were performed on a 7900HT Fast Real-Time PCR instrument with probes and reagents purchased from Applied Biosystems.

DNA sequencing. The 58 kb interval between rs12555547 and rs10965244 was sequenced in two individuals homozygous for the risk allele, and in one individual homozygous for the wild-type allele as described (S7). The coding region and flanking intronic sequences of CDKN2A and CDKN2B were sequenced in 96 arbitrarily selected Caucasian men. All sequence variants identified were verified by manual inspection of the chromatograms and missense changes were confirmed by an independent resequencing reaction.

Reverse transcription and PCR Amplification of cDNAs. RNA was isolated from human, placenta, and EBV-transformed lymphocytes by a modified phenol-chloroform extraction (TRIZOL reagent, Invitrogen Corporation, Carlsbad, Calif.), and reverse transcribed (SuperScript III First-strand synthesis system, Invitrogen). Aliquots of cDNA were amplified using primers directed against spliced ESTs CN277071, BX100299 and DQ485453.

Statistical Analysis. For the genome-wide scan, allelic associations were evaluated for each SNP using chi-square tests on 2×2 contingency tables with no adjustments. Calculations were performed independently at Perlegen Sciences and at UT Southwestern and essentially identical results were obtained. To determine the empirical P-values we randomized the sample case/control status 1,000 times, and calculated allelic associations on each permuted dataset. SNPs that were significantly associated with CHD in the genome-wide scan were assayed in a second set of cases and controls and analyzed using Chi-square tests and permutation testing. For the remaining data sets, case-control differences in allele frequencies of rs10757274 and rs2383206 were evaluated using chi-square tests on 3×2 contingency tables. Population attributable risk was calculated using the formula $PAR=I(T)-I(0)$, where $I(T)$ is the total disease incidence in the population, and $I(0)$ is the disease incidence in unexposed individuals.

NOTES

1. C. J. Murray, A. D. Lopez, *Lancet* 349, 1436 (1997).
2. C. D. Mathers, D. Loncar, *PLoS Med* 3, e442 (2006).
3. S. F. Saccone et al., *Hum Mol Genet* 16, 36 (2007).
4. The ARIC Study Investigators, *Am J Epidemiol* 129, 687 (1989).
5. Schnohr, Jensen, Scharling, M. Appleyard, *Eur Heart J* 3, Suppl H., H1 (2001).
6. R. G. Victor et al., *Am J Cardiol* 93, 1473 (2004).
7. A. S. Agatston et al., *J Am Coll Cardiol* 15, 827 (1990).
8. Pasmant, Laurendeau, Heron, Vidaud, Vidaud, Bieche, *Cancer Res* 67, 1 (2007).
9. J. Cohen et al., *Proc Natl Acad Sci USA* 103, 1810 (2006).
10. Cohen, Boerwinkle, T. H. Mosley, H. H. Hobbs, *N. Engl. J. Med.* 354, 34 (2006).
11. S. Romeo et al., *Nat Genet* 39, 513 (2007).
12. *Circulation* 106, 3143 (2002).
S1. The ARIC Study Investigators, *Am J Epidemiol* 129, 687 (1989).
S2. L. E. Chambless et al., *J Clin Epidemiol* 56, 880 (2003).
S3. S. A. Brown et al., *Arterioscler. Thromb* 13, 1139 (1993).
S4. Schnohr, Jensen, Scharling, Appleyard, *Eur Heart J* 3, Suppl H., H1 (2001).
S5. T. Jain et al., *J. Am Coll Cardiol* 44, 1011 (2004, 2004).
S6. N. Patil et al., *Science* 294, 1719 (2001).
S7. M. Tartaglia et al., *Nat Genet* 39, 75 (2007).

TABLE 1

Study design for identification and validation of sequence variants associated with coronary heart disease. Assuming independence, the probability of any single SNP achieving a nominal significance level of 0.025 in all three studies with the associations being in the same direction was $3.9 \times 10^{-6}$ ($0.025^3 \times 0.5^2$), thus none of the 100,000 SNPs would be expected by chance to replicate consistently in all three comparisons.

Screening
Genome-wide Association Scan (75,000 SNPs/person)
Ottawa Heart Study-1 (OHS-1)
322 Cases:312 controls Replicate Association Study 1:SNPs with P < 0.025
Ottawa Heart Study-2 (OHS-2)
311 cases:326 controls Replicate Association Study 2:SNPs with P < 0.025
Atherosclerosis Risk in Communities Study (ARIC)
1,347 cases:9,054 controls rs10757274 and rs2383206

Validation

| Copenhagen City Heart Study(CCHS) | Dallas Heart Study (DHS) | Ottawa Heart Study-3 (OHS-3) |
|---|---|---|
| 1,525 cases | 154 cases | 618 cases |
| 9,053 controls | 527 controls | 782 controls |

TABLE 2

Association between SNPs rs10757274 and rs2383206 and CHD.

| | rs10757274 | | | | | | | | rs2383206 | | | | | | | |
|---|---|---|---|---|---|---|---|---|---|---|---|---|---|---|---|---|
| | Controls | | | Cases | | | | | Controls | | | Cases | | | | |
| Cohort | AA | AG | GG | AA | AG | GG | $\chi^2$-P | HW-P | AA | AG | GG | AA | AG | GG | $\chi^2$-P | HW-P |
| OHS-1 | 85 | 149 | 78 | 49 | 148 | 125 | $3.7 \times 10^{-6}$ | 0.08 | 77 | 147 | 88 | 45 | 140 | 137 | $6.7 \times 10^{-6}$ | 0.19 |
| OHS-2 | 85 | 161 | 80 | 56 | 140 | 108 | 0.0009 | 0.4 | 80 | 160 | 86 | 50 | 141 | 113 | 0.0008 | 0.34 |
| ARIC | 2063 | 3822 | 1858 | 230 | 525 | 282 | 0.004 | 0.11 | 2140 | 4161 | 2231 | 230 | 600 | 324 | 0.0007 | 0.21 |
| CCHS | 2752 | 4543 | 1758 | 393 | 792 | 340 | 0.0004 | 0.56 | 2489 | 4583 | 1981 | 372 | 782 | 371 | 0.016 | 0.58 |
| DHS | 147 | 258 | 122 | 27 | 85 | 42 | 0.025 | 0.99 | 131 | 258 | 138 | 24 | 84 | 46 | 0.045 | 0.95 |
| OHS-3 | 228 | 418 | 201 | 121 | 333 | 193 | 0.0003 | 0.96 | 197 | 416 | 229 | 115 | 327 | 209 | 0.011 | 0.98 |

Values are numbers of individuals in each genotype group.

P-values were calculated by Chi-Square tests on allele counts.

OHS, Ottawa Heart Study;

ARIC, Atherosclerosis Risk in Communities Study;

CCHS, Copenhagen City Heart Study;

DHS, Dallas Heart Study;

SNP, single nucleotide polymorphism.

TABLE 3

Risk of CHD as a function of rs10757274 and rs2383206 in the Atherosclerosis Risk in Communities Study and the Copenhagen City Heart Study.

| | Atherosclerosis Risk in Communities Study | | | | | Copenhagen City Heart Study | | | | |
|---|---|---|---|---|---|---|---|---|---|---|
| | | Number of Events | | | | | Number of Events | | | |
| | n (%) | Observed | Expected[1] | Incidence[2] | Hazard Ratio | n (%) | Observed | Expected | Incidence | Hazard Ratio |
| | | | | rs10757274 | | | | | | |
| AA | 2,293 (26) | 255[3] | 295 | 79 (70-89) | 1 | 3,145 (30) | 393[5] | 473 | 61 (55-68) | 1 |
| AG | 4,347 (50) | 564 | 553 | 93 (86-101) | 1.18 (1.02-1.37) | 5,335 (50) | 792 | 755 | 73 (68-79) | 1.26 (1.12-1.42) |
| GG | 2,140 (24) | 298 | 269 | 101 (90-114) | 1.29 (1.09-1.52) | 2,098 (20) | 340 | 296 | 80 (72-89) | 1.38 (1.19-1.60) |
| | | | | rs2383206 | | | | | | |
| AA | 2,370 (25) | 259[4] | 310 | 78 (69-88) | 1 | 2,861 (27) | 372[6] | 425 | 64 (58-71) | 1 |
| AG | 4,761 (49) | 643 | 610 | 97 (90-105) | 1.26 (1.09-1.46) | 5,365 (51) | 782 | 772 | 72 (67-77) | 1.16 (1.02-1.31) |
| GG | 2,555 (26) | 345 | 327 | 97 (88-108) | 1.26 (1.07-1.48) | 2,352 (22) | 371 | 327 | 78 (71-87) | 1.29 (1.12-1.50) |

[1] Based on the Log-rank test.
[2] Incidence rate measured in number of events per 10,000 person years of follow-up.
[3] $p < 0.0111$
[4] $p < 0.0041$.
[5] $p < 0.00001$.
[6] $p < 0.0$

TABLE 4

Sequence variations identified in the 58 kd risk interval on chromosome 9 in two individuals homozygous for the risk allele and one homozygous for the alternate allele.

| | | Allele | | Risk Genotype | | Referent Genotype |
|---|---|---|---|---|---|---|
| Position | Type | Major | Minor | 1 | 2 | 1 |
| 22062264 | SNP | A | G | G/G | G/G | A/A |
| 22062301 | SNP | G | C | C/C | C/C | G/G |
| 22062638 | SNP | G | A | A/A | A/A | G/G |
| 22062719 | SNP | A | G | G/G | G/G | A/A |
| 22063996 | SNP | T | G | G/G | G/G | N/N |
| 22067543 | SNP | C | T | T/T | T/T | N/N |
| 22071397 | SNP | G | T | T/T | T/T | G/G |
| 22071850 | SNP | C | T | T/T | T/T | C/C |
| 22072375 | SNP | A | C | A/C | A/A | A/A |
| 22073209 | SNP | C | T | C/C | C/T | N/N |
| 22073400 | SNP | A | T | A/T | A/A | N/N |
| 22073404 | SNP | C | T | T/T | T/T | N/N |
| 22074310 | SNP | C | T | T/T | T/T | N/N |
| 22075598 | SNP | T | C | C/C | C/C | N/N |
| 22077473 | SNP | T | C | C/C | C/C | C/T |
| 22078090 | SNP | A | T | T/T | T/T | A/A |
| 22078094 | SNP | A | G | G/G | G/G | A/A |
| 22078260 | SNP | C | T | T/T | T/T | C/C |
| 22078465 | DEL | CA | | —/ | —/— | CA/CA |
| 22089568 | SNP | C | A | A/A | A/A | N/N |
| 22089755 | INS | — | A | A/A | A/A | —/ |
| 22090176 | SNP | G | C | C/C | C/C | G/G |
| 22091702 | SNP | T | C | C/C | C/C | T/T |
| 22092165 | SNP | C | T | T/T | T/T | C/C |
| 22092437 | SNP | G | A | G/G | G/G | A/G |
| 22093183 | SNP | G | T | T/T | T/T | G/G |
| 22093341 | SNP | T | G | G/G | G/G | T/T |
| 22093813 | SNP | A | G | G/G | G/G | A/A |
| 22095927 | SNP | T | C | C/C | C/C | T/T |
| 22096225 | SNP | G | A | A/A | A/A | N/N |
| 22096271 | SNP | A | G | G/G | G/G | N/N |
| 22096400 | SNP | G | A | A/G | G/G | N/N |
| 22096731 | SNP | T | A | A/A | A/A | T/T |
| 22097238 | SNP | A | T | A/A | A/A | A/T |
| 22100131 | SNP | T | C | C/C | C/C | T/T |
| 22101587 | INS | --- | TTGAT | TTGAT/TTGAT | TTGAT/TTGAT | —/— |
| 22102241 | SNP | A | C | C/C | C/C | A/A |
| 22102427 | SNP | A | G | G/G | G/G | A/A |
| 22102599 | SNP | T | C | C/C | C/C | N/N |
| 22104469 | SNP | G | C | C/C | C/C | G/G |
| 22104495 | SNP | A | G | G/G | G/G | A/A |
| 22105026 | SNP | A | G | G/G | G/G | A/A |
| 22105286 | SNP | T | C | C/C | C/C | T/T |
| 22105589 | SNP | A | T | T/T | T/T | N/N |
| 22105959 | SNP | A | G | G/G | G/G | A/G |
| 22106046 | SNP | A | G | G/G | G/G | A/A |
| 22106071 | SNP | T | C | C/C | C/C | C/T |
| 22106220 | SNP | T | C | C/C | C/C | T/T |
| 22107781 | SNP | C | T | C/T | C/C | C/C |
| 22110491 | INS | — | T | T/T | T/T | —/ |
| 22110813 | DEL | CAT | | —/ | —/ | CAT/— |
| 22113766 | SNP | A | C | C/C | C/C | A/A |
| 22114123 | SNP | T | A | A/A | A/A | T/T |
| 22114140 | SNP | A | T | T/T | T/T | A/A |
| 22115347 | SNP | A | C | C/C | C/C | A/A |
| 22115503 | SNP | G | C | C/C | C/C | G/G |
| 22115913 | SNP | C | T | T/T | T/T | N/N |
| 22117613 | SNP | C | T | C/T | C/C | C/C |
| 22117641 | SNP | G | A | A/G | G/G | G/G |
| 22117879 | SNP | A | G | A/G | A/G | A/A |
| 22118166 | INS | | AT | AT/— | AT/— | —/ |
| 22118600 | SNP | G | A | A/G | A/G | N/N |
| 22118730 | SNP | C | G | C/G | C/C | N/N |
| 22119594 | SNP | G | C | C/C | C/C | C/C |
| 22119724 | INS | — | T | T/T | T/— | T/T |
| 22120389 | SNP | A | T | A/T | A/T | A/A |

TABLE 5

Allele frequencies of chromosome 9 sequence variants associated with CHD in Caucasians. Minor Allele Frequency

| SNP ID | Position | Caucasians | African-Americans |
|---|---|---|---|
| rs9632884 | 22062301 | 0.48 | 0.008 |
| rs6475606 | 22071850 | 0.5 | 0.008 |
| rs10757272 | 22078260 | 0.5 | 0.15 |
| rs10757274 | 22086055 | 0.49 | 0.21 |
| rs4977574 | 22088574 | 0.5 | 0.08 |
| rs2891168 | 22088619 | 0.5 | 0.08 |
| rs1333042 | 22093813 | 0.49 | 0.008 |
| rs2383206 | 22105026 | 0.49 | 0.41 |
| rs1333048 | 22115347 | 0.49 | 0.25 |
| rs1333049 | 22115503 | 0.49 | 0.175 |

TABLE 6

Association between rs10757274 and 2383206 and CHD in African-Americans in ARIC and DHS.

| | rs10757274 | | | | | | | rs2383206 | | | | | | |
|---|---|---|---|---|---|---|---|---|---|---|---|---|---|---|
| | Controls | | | Cases | | | | Controls | | | Cases | | | |
| Cohort | AA | AG | GG | AA | AG | GG | P | AA | AG | GG | AA | AG | GG | P |
| ARIC | 1857 | 971 | 143 | 187 | 92 | 14 | 0.90 | 1019 | 1532 | 541 | 114 | 161 | 46 | 0.32 |
| DHS | 447 | 251 | 32 | 175 | 66 | 21 | 0.64 | 231 | 371 | 129 | 90 | 123 | 48 | 0.67 |

Values in the table are numbers of individuals.
P values were calculated using Chi-square tests.
ARIC, Atherosclerosis Risk in Communities Study;
DHS, Dallas Heart Study.
Cases and controls are defined as indicated herein.

What is claimed is:

1. A method for detecting risk for coronary atherosclerosis in a human, comprising:
    detecting in a nucleic acid sample obtained from the human or a genotype derived from the human the presence of an allele associated with increased risk for coronary atherosclerosis wherein the allele is the presence of a "G" at the position of human chromosome 9 identified by rs10757274 or rs2383206; and
    treating the human thus characterized for increased risk for coronary atherosclerosis with therapy to delay onset of or slow progression of the coronary atherosclerosis.

2. The method of claim 1, wherein detecting is performed using allele-specific hybridization, allele-specific PCR, sequencing, oligonucleotide microarray analysis or mass spectrophotometry.

3. The method of claim 1, wherein the human is evaluated for the human's medical history, family history, age, gender, socio-economic status, race, ethnicity, smoking, plasma cholesterol levels, plasma triglyceride levels, plasma lipids, plasma glucose, plasma insulin, plasma lipoproteins, or coronary artery calcification using electron-beam computer tomography.

4. The method of claim 1 wherein the therapy comprises a lipid-lowering medication.

5. The method of claim 2 wherein the therapy comprises a lipid-lowering medication.

6. The method of claim 3 wherein the therapy comprises a lipid-lowering medication.

7. The method of claim 1 wherein the allele is a single nucleotide polymorphism at the position of human chromosome 9 identified by rs10757274.

8. The method of claim 2 wherein the allele is a single nucleotide polymorphism at the position of human chromosome 9 identified by rs10757274.

9. The method of claim 3 wherein the allele is a single nucleotide polymorphism at the position of human chromosome 9 identified by rs10757274.

10. The method of claim 4 wherein the allele is a single nucleotide polymorphism at the position of human chromosome 9 identified by rs10757274.

11. A method of genotyping a nucleic acid sample from a human at risk for, or diagnosed with, coronary heart disease, comprising determining the presence of a "G" allele at the position of human chromosome 9 identified by rs10757274 or rs2383206 and further comprising the step of treating the human with therapy to delay onset of or slow progression of the coronary atherosclerosis.

12. The method of claim 11, wherein genotyping is performed using allele-specific hybridization, allele-specific PCR, sequencing, oligonucleotide microarray analysis or mass spectrophotometry.

13. The method of claim 11, wherein the human is evaluated for the human's medical history, family history, age, gender, socio-economic status, race, ethnicity, smoking, plasma cholesterol levels, plasma triglyceride levels, plasma lipids, plasma glucose, plasma insulin, plasma lipoproteins, or coronary artery calcification using electron-beam computer tomography.

14. The method of claim 11, wherein the therapy comprises a lipid-lowering medication.

15. The method of claim 12, wherein the therapy comprises a lipid-lowering medication.

16. The method of claim 13, wherein the therapy comprises a lipid-lowering medication.

17. The method of claim 11 wherein the allele is a single nucleotide polymorphism at the position of human chromosome 9 identified by rs10757274.

18. The method of claim 12 wherein the allele is a single nucleotide polymorphism at the position of human chromosome 9 identified by rs10757274.

19. The method of claim 13 wherein the allele is a single nucleotide polymorphism at the position of human chromosome 9 identified by rs10757274.

20. A method of determining that a person carries an allele associated with increased risk for coronary atherosclerosis, the method comprising:

determining that the person has an RA-CHR9 allele, wherein the allele is the presence of a "G" at the position of human chromosome 9 identified by rs10757274 or rs2383206; and treating the person thus characterized for increased risk for coronary atherosclerosis with therapy to delay onset of or slow progression of the coronary atherosclerosis.

21. The method of claim 20 wherein the determining step comprises detecting the allele using a method selected from the group consisting of: mass spectroscopy, oligonucleotide microarray analysis, allele-specific hybridization, allele-specific PCR, and sequencing.

22. The method of claim 20, wherein the human is evaluated for the human's medical history, family history, age, gender, socio-economic status, race, ethnicity, smoking, plasma cholesterol levels, plasma triglyceride levels, plasma lipids, plasma glucose, plasma insulin, plasma lipoproteins, or coronary artery calcification using electron-beam computer tomography.

23. The method of claim 20 wherein the therapy comprises a lipid-lowering medication.

24. The method of claim 21 wherein the therapy comprises a lipid-lowering medication.

25. The method of claim 22 wherein the therapy comprises a lipid-lowering medication.

26. The method of claim 20 wherein the allele is a single nucleotide polymorphism at the position of human chromosome 9 identified by rs10757274.

27. The method of claim 21 wherein the allele is a single nucleotide polymorphism at the position of human chromosome 9 identified by rs10757274.

28. The method of claim 22 wherein the allele is a single nucleotide polymorphism at the position of human chromosome 9 identified by rs10757274.

29. The method of claim 23 wherein the allele is a single nucleotide polymorphism at the position of human chromosome 9 identified by rs10757274.

* * * * *

UNITED STATES PATENT AND TRADEMARK OFFICE
CERTIFICATE OF CORRECTION

| | | |
|---|---|---|
| PATENT NO. | : 7,883,851 B2 | Page 1 of 1 |
| APPLICATION NO. | : 11/751563 | |
| DATED | : February 8, 2011 | |
| INVENTOR(S) | : Jonathan C. Cohen et al. | |

It is certified that error appears in the above-identified patent and that said Letters Patent is hereby corrected as shown below:

On the title page, item [75]
The second inventor's last name is spelled "Hobbs".

Signed and Sealed this
Twenty-second Day of March, 2011

David J. Kappos
*Director of the United States Patent and Trademark Office*